(12) United States Patent
Atallah et al.

(10) Patent No.: US 11,904,224 B2
(45) Date of Patent: Feb. 20, 2024

(54) SYSTEM AND METHOD FOR CLIENT-SIDE PHYSIOLOGICAL CONDITION ESTIMATIONS BASED ON A VIDEO OF AN INDIVIDUAL

(71) Applicant: KONINKLIJKE PHILIPS N.V., Eindhoven (NL)

(72) Inventors: Louis Nicolas Atallah, Boston, MA (US); Joseph James Frassica, Gloucester, MA (US); Minnan Xu, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 739 days.

(21) Appl. No.: 16/969,114

(22) PCT Filed: Jan. 31, 2019

(86) PCT No.: PCT/EP2019/052311
§ 371 (c)(1),
(2) Date: Aug. 11, 2020

(87) PCT Pub. No.: WO2019/162054
PCT Pub. Date: Aug. 29, 2019

(65) Prior Publication Data
US 2021/0038088 A1  Feb. 11, 2021

Related U.S. Application Data

(60) Provisional application No. 62/632,510, filed on Feb. 20, 2018.

(51) Int. Cl.
*G16H 40/67* (2018.01)
*A63B 71/06* (2006.01)
(Continued)

(52) U.S. Cl.
CPC .............. *A63B 71/06* (2013.01); *A61B 3/112* (2013.01); *A61B 5/0077* (2013.01);
(Continued)

(58) Field of Classification Search
CPC ........ A63B 71/06; G16H 40/67; G16H 50/30; G06V 20/46; G06V 20/41; A61B 5/0077;
(Continued)

(56) References Cited

U.S. PATENT DOCUMENTS 9,125,606 B2   9/2015 Verkruijsse
9,770,197 B2   9/2017 Bresch
(Continued)

FOREIGN PATENT DOCUMENTS

WO   199628086 A1   9/1996
WO   2015126858 A1  8/2015
(Continued)

OTHER PUBLICATIONS

International Search Report and Written Opinion of PCT/EP2019/052311, dated May 27, 2019.
(Continued)

*Primary Examiner* — Carl H Layno
*Assistant Examiner* — Michael J Lau

(57) ABSTRACT

The present disclosure pertains to a system for providing client-side physiological condition estimations during a live video session. In some embodiments, the system includes a first client computer system that is caused to: (i) store a neural network on one or more computer-readable storage media of the first client computer system, (ii) obtain a live video stream of an individual via a camera of the first client computer system during a video streaming session between the first client computer system and a second client computer system, (iii) provide, during the video streaming session, video data of the live video stream as input to the
(Continued)

neural network to obtain physiological condition information from the neural network, and (iv) provide, during the video streaming session, the physiological condition information for presentation at the second client computer system.

18 Claims, 5 Drawing Sheets

(51) Int. Cl.
*G16H 50/30* (2018.01)
*A61B 3/11* (2006.01)
*A61B 5/00* (2006.01)
*A61B 5/0205* (2006.01)
*A61B 5/103* (2006.01)
*A61B 5/11* (2006.01)
*A61B 5/1455* (2006.01)
*A61B 5/16* (2006.01)
*G06N 3/082* (2023.01)
*G06T 11/00* (2006.01)
*G10L 25/30* (2013.01)
*G10L 25/63* (2013.01)
*G10L 25/66* (2013.01)
*H04N 7/14* (2006.01)
*G06V 20/40* (2022.01)
*G06F 18/21* (2023.01)
*A61B 5/024* (2006.01)
*A61B 5/08* (2006.01)

(52) U.S. Cl.
CPC .......... *A61B 5/0205* (2013.01); *A61B 5/1032* (2013.01); *A61B 5/1101* (2013.01); *A61B 5/14551* (2013.01); *A61B 5/165* (2013.01); *A61B 5/4803* (2013.01); *A61B 5/7267* (2013.01); *G06F 18/21* (2023.01); *G06N 3/082* (2013.01); *G06T 11/00* (2013.01); *G06V 20/41* (2022.01); *G06V 20/46* (2022.01); *G10L 25/30* (2013.01); *G10L 25/63* (2013.01); *G10L 25/66* (2013.01); *G16H 40/67* (2018.01); *G16H 50/30* (2018.01); *H04N 7/141* (2013.01); *A61B 5/02444* (2013.01); *A61B 5/0816* (2013.01)

(58) Field of Classification Search
CPC ... A61B 5/0205; A61B 5/1032; A61B 5/1101; A61B 5/14551; A61B 5/165; A61B 5/4803; A61B 5/7267; A61B 5/02444; A61B 5/0816; A61B 3/112; G06N 3/082; G06T 11/00; G10L 25/30; G10L 25/63; G10L 25/66; H04N 7/141

USPC ....................................................... 600/301
See application file for complete search history.

(56) References Cited

U.S. PATENT DOCUMENTS

| 9,980,666 | B2 | 5/2018 | Bresch | |
| 2010/0201999 | A1* | 8/2010 | Sasaki | H04N 1/6058 358/1.9 |
| 2011/0295597 | A1 | 12/2011 | Brady | |
| 2014/0192177 | A1 | 7/2014 | Bartula | |
| 2014/0253709 | A1 | 9/2014 | Bresch | |
| 2014/0257852 | A1* | 9/2014 | Walker | G06Q 10/10 705/3 |
| 2015/0134107 | A1* | 5/2015 | Hyde | G16H 20/13 700/237 |
| 2015/0154002 | A1* | 6/2015 | Weinstein | G06F 9/451 715/728 |
| 2015/0261930 | A1 | 9/2015 | Espinosa Escalona | |
| 2015/0305662 | A1 | 10/2015 | Kilmer | |
| 2016/0063893 | A1* | 3/2016 | Kanuganti | H04N 21/8545 348/62 |
| 2016/0092721 | A1 | 3/2016 | Kanagasingam | |
| 2016/0283860 | A1* | 9/2016 | Pycock | H04N 21/4788 |
| 2016/0295165 | A1 | 10/2016 | Mizuhara | |
| 2017/0124276 | A1* | 5/2017 | Tee | G08B 21/0446 |
| 2017/0181667 | A1 | 6/2017 | Gettelman | |
| 2017/0238842 | A1 | 8/2017 | Jacquel | |

FOREIGN PATENT DOCUMENTS

| WO | 2018031949 A1 | 2/2018 | |
| WO | WO-2018031949 A1 * | 2/2018 | ......... G06F 16/9535 |

OTHER PUBLICATIONS

"Real-Time Data for Real-time Care", Dictum Health, Telehealth Medical Equipment, Telehealth Solution 2017.
Koch, Sabine "Home telehealth—Current state and future trends," International Journal of Meical Informatics, vol. 75, No. 8, pp. 565-576, Aug. 2006. Abstract Only.
"MSF Telemedicine Brings Care to Patients in Remote Areas," MSF USA, Jun. 22, 2016. [Online]. Available: http://www.doctorswithoutborders.org/article/msf-telemedicine-brings-care-patients-remote-areas. [Accessed: Mar. 28, 2017].
"Telehealth services becoming popular with US consumers and insurers," Reuters, Dec. 23, 2015.
Verkruysse, Wim et al."Calibration of Contactless Pulse Oximetry," Anethesia-Analgesia, vol. 124, No. 1, pp. 136-145, Jan. 2017.
Höfle, Marion et al "You can see pain in the eye: Pupillometry as an index of pain intensity under different luminance conditions," Int. J. Psychophysiol, vol. 70, No. 3, pp. 171-175, Dec. 2008. Abstract Only.

* cited by examiner

SYSTEM AND METHOD FOR CLIENT-SIDE PHYSIOLOGICAL CONDITION ESTIMATIONS BASED ON A VIDEO OF AN INDIVIDUAL

BACKGROUND

1. Field

The present disclosure pertains to facilitating physiological condition estimations based on a video of an individual.

2. Description of the Related Art

Telemedicine services facilitate clinicians and nurses to treat patients via video. Telemedicine may be utilized as a form of an early triage for more serious conditions or provide care for patients where care is not accessible. Although computer-assisted telemedicine systems exist, such systems may not facilitate an accurate assessment of an individual's vital signs during a consultation session. For example, prior art systems may require the patient to wear a plurality of sensors (each of which has to be individually powered and maintained), and measurements may not done in real time. These and other drawbacks exist.

SUMMARY

Accordingly, one or more aspects of the present disclosure relate to a system configured to provide client-side physiological condition estimations during a live video session. The system comprises a first client computer system including a camera, one or more computer-readable storage media, and one or more first processors configured by machine readable instructions that cause the first client computer system to: store a neural network on the one or more computer-readable storage media of the first client computer system, the neural network being trained on audio, image, or video data to estimate physiological conditions; obtain a live video stream of an individual via the camera during a video streaming session between the first client computer system and a second client computer system; provide, during the video streaming session, video data of the live video stream as input to the neural network to obtain physiological condition information from the neural network, the physiological condition information indicating one or more physiological conditions of the individual; and provide, during the video streaming session, the physiological condition information for presentation at the second client computer system.

Yet another aspect of the present disclosure relates to a method of providing client-side physiological condition estimations during a live video session. The method comprises: storing a machine learning model on one or more computer-readable storage media of a first client computer system, the machine learning model being trained on audio, image, or video data to estimate physiological conditions; obtaining a live video stream of an individual via a camera of the first client computer system during a video streaming session between the first client computer system and a second client computer system; providing, during the video streaming session, video data of the live video stream as input to the machine learning model to obtain physiological condition information from the machine learning model, the physiological condition information indicating one or more physiological conditions of the individual; and providing, during the video streaming session, the physiological condition information for presentation at the second client computer system.

Still another aspect of present disclosure relates to a system for providing client-side physiological condition estimations during a live video session. The system comprises: means for storing a machine learning model on a first client computer system, the machine learning model being trained on audio, image, or video data to estimate physiological conditions; means for obtaining a live video stream of an individual at the first client computer system during a video streaming session between the first client computer system and a second client computer system; means for providing, during the video streaming session, video data of the live video stream as input to the machine learning model to obtain physiological condition information from the machine learning model, the physiological condition information indicating one or more physiological conditions of the individual; and means for providing, during the video streaming session, the physiological condition information for presentation at the second client computer system.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
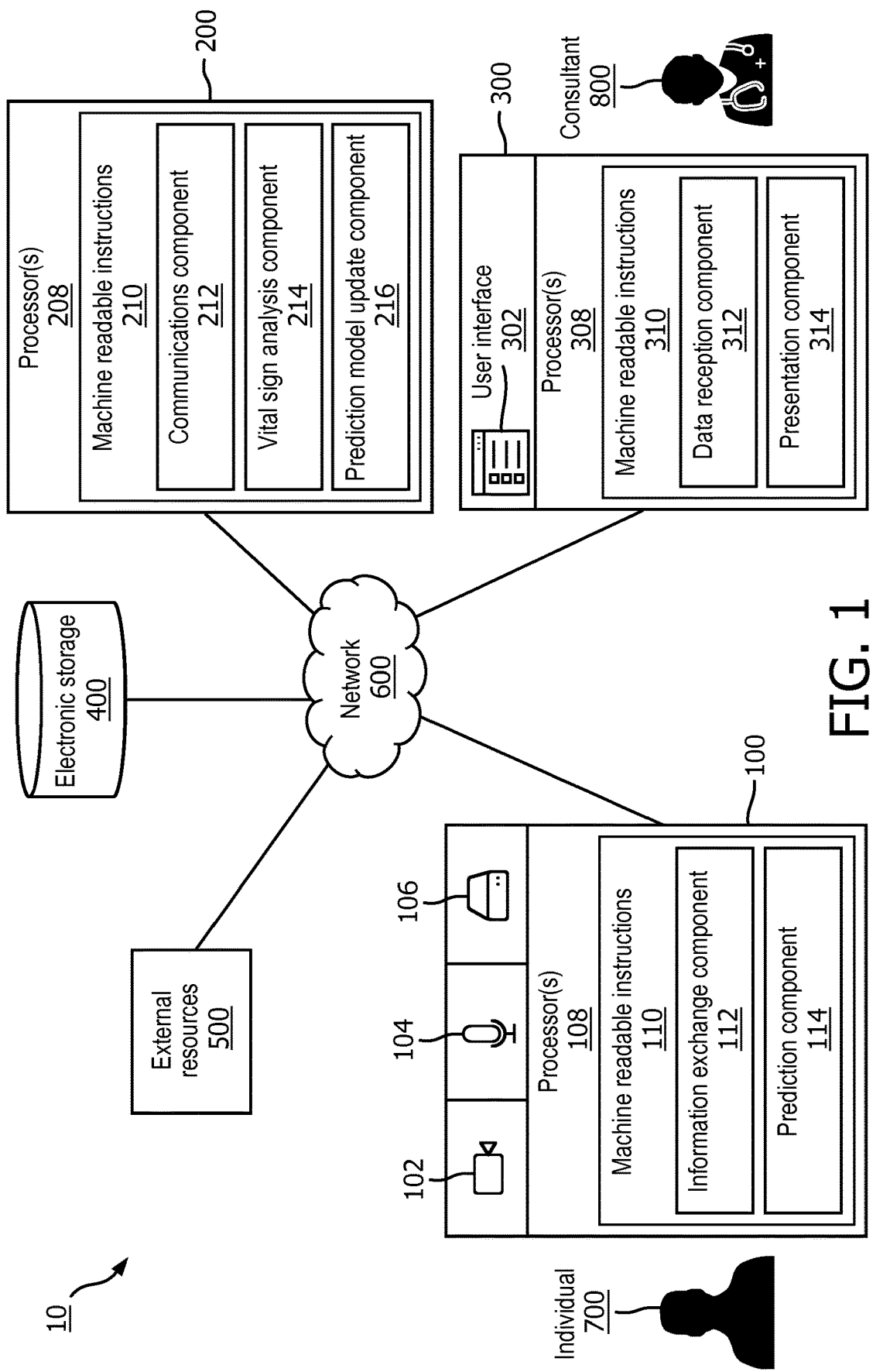
FIG. 1 is a schematic illustration of a system configured to provide physiological condition estimations based on a video stream, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
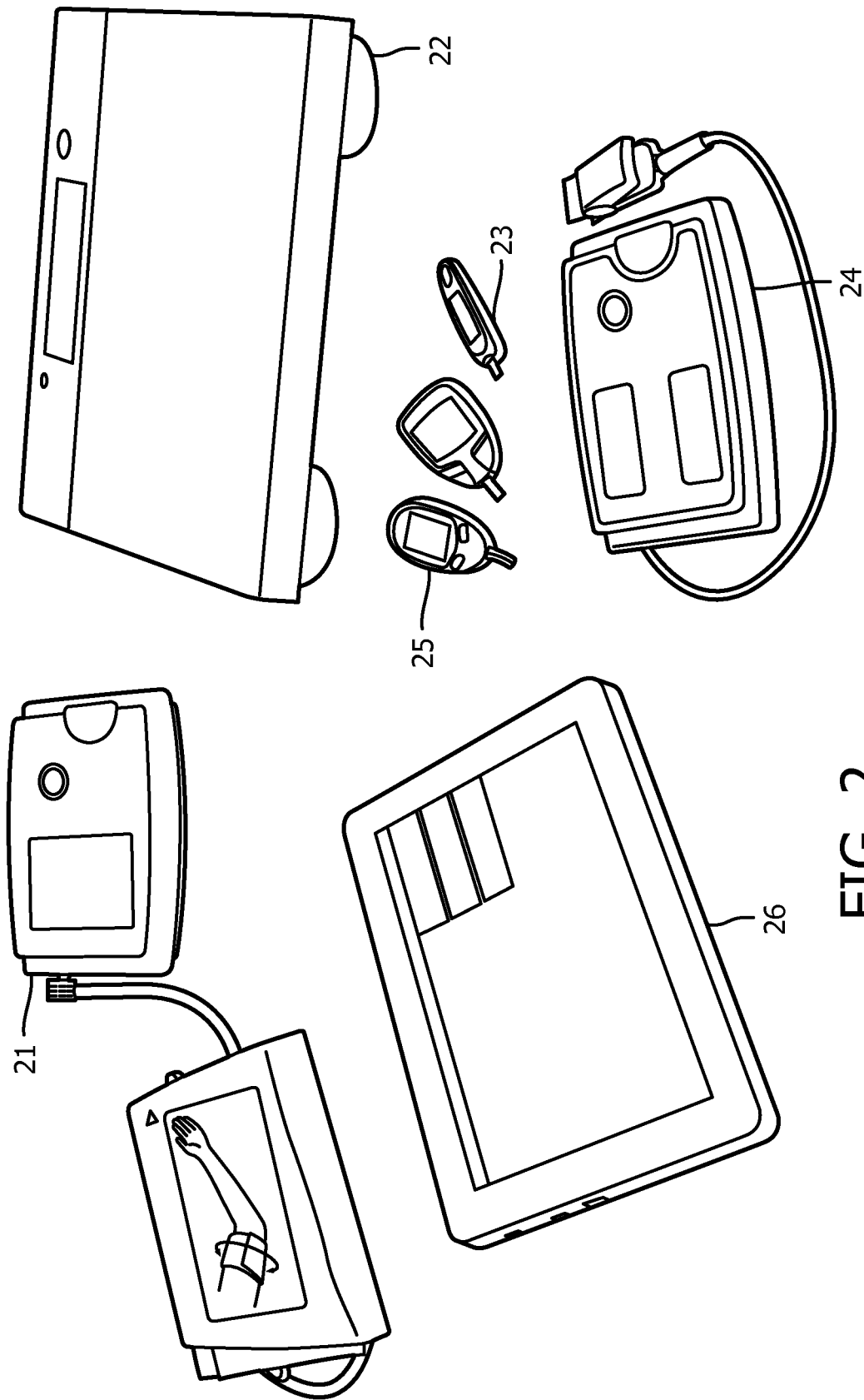
FIG. 2 illustrates a plurality of sensors facilitating vital sign measurements, in accordance with one or more embodiments.

FIG. 1 is a schematic illustration of a system 10 for providing physiological condition estimations based on a video stream, in accordance with one or more embodiments. In some embodiments, an individual (e.g., a patient) may utilize one or more sensors to obtain information related to one or more physiological conditions (e.g., vital signs). In some embodiments, such sensors may be individually worn and/or utilized to obtain one or more measurements, and the aggregated measurement data may be electronically provided to a clinician to assist in their decision making/diagnosis. By way of a non-limiting example, FIG. 2 illustrates a plurality of sensors facilitating vital sign measurements, in accordance with one or more embodiments. As shown in FIG. 2, traditional sensors such as a blood pressure cuff 21, a weight scale 22, a thermometer 23, an SPO2 sensor 24, and a glucose monitor 25 may be utilized by an individual to obtain information related to their physiological conditions prior to and/or during a consultation session and the measurement results may be reported to a consultant (e.g., a clinician) electronically and/or verbally during a consultation session. In addition, a computer system 26 (e.g., laptop, tablet, smartphone, etc.) may provide a 2-way video interaction between the consultant and the individual. However, unlike a visit to the doctor's, many of measurements obtained by the individual may not done in real time, resulting in inaccurate measurements and/or diagnosis. In some embodiments, vital signs of a subject may be determined via a camera and one or more (attachable) sensors as described in U.S. patent application Ser. No. 14/173,117, filed Feb. 5, 2014, entitled "SYSTEM AND METHOD FOR DETERMINING A VITAL SIGN OF A SUBJECT", the content of which is incorporated herein in its entirety by reference.

Returning to FIG. 1, system 10 is configured to utilize existing camera and voice during a telehealth application to provide a set of vitals (e.g., in real time). In some embodiments, system 10 is configured to facilitate real time presentation of the set of vital signs to a clinician as a patient is speaking to the clinician. In some embodiments, system 10 is configured to facilitate (i) automatic detection of breathing difficulties, (ii) automated detection of emotional stress/pain in real time, (iii) automated detection of physiological changes, (iv) automatic detection of a change in vitals and/or physiological features due to a certain request and/or activity, (v) trending of vital signs and/or physiological conditions and comparing the trends to previous consultations, (vi) automated calibration for skin color, (vii) automatic analysis of recorded video, and/or other features.

In some embodiments, system 10 is configured to facilitate estimation of one or more physiological conditions. In some embodiments, system 10 may estimate one or more physiological conditions and/or changes to the one or more physiological conditions based on previous measurements obtained by the individual. In some embodiments, the estimations may be based on data corresponding to one or more other patients (i) having similar conditions and/or symptoms, (ii) having similar medical interventions, (iii) being within a predetermined geographical area, or having other criteria. In some embodiments, the estimations may be based on one or more regressions (e.g., linear), machine learning model outputs, and/or other information.

In some embodiments, remote monitoring systems may transmit live audio, image, or video data of the individual (e.g., via a wired and/or wireless network) to a server, at which one or more physiological conditions may be estimated. The estimations may be facilitated, via one or more prediction models (e.g., neural network, other machine learning models, etc.), by analyzing the audio, image, or video data of the individual. However, such systems' results may be inaccurate and/or limited due to bandwidth limitations, internet speed limitations, inferior audio, image, or video quality, server load, and/or other factors. Accordingly, system 10 is configured to obtain video data of an individual from a camera on a client computer system associated with the individual and determine the one or more physiological conditions of the individual on the client computer system. In some embodiments, system 10 is configured to obtain and store a prediction model on the client computer system and provide the audio, image, or video data as input to the prediction model to obtain physiological condition information from the prediction model. Such prediction models may include neural networks, other machine learning models, or other prediction models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it is allowed to propagate to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

In some embodiments, system 10 comprises a first client computer system 100 (e.g., associated with individual 700), a server computer system 200, a second client computer system 300 (e.g., associated with consultant 800), electronic storage 400, external resources 500, network 600, or other components.

Electronic storage 400 comprises electronic storage media that electronically stores information (e.g., a patient profile indicative of vital signs and/or video data associated with individual 700.). The electronic storage media of electronic storage 400 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 400 may be (in whole or in part) a separate component within system 10, or electronic storage 400 may be provided (in whole or in part) integrally with one or more other components of system 10 (e.g., first client computer system 100, server computer system 200, etc.). In some embodiments, electronic storage 400 may be located in a server together with server computer system 200, in a server that is part of external resources 500, and/or in other locations. Electronic storage 400 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 400 may store software algorithms, information determined by first client computer system 100, information received via server computer system 200 and/or graphical user interface 302 and/or other external computing systems, information received from external resources 500, and/or other information that enables system 10 to function as described herein.

External resources 500 include sources of information and/or other resources. For example, external resources 500 may include individual 700's electronic medical record (EMR), other patients' electronic health record (EHR), or other information. In some embodiments, external resources 500 include health information related to individual 700. In some embodiments, the health information comprises demographic information, vital signs information, medical condition information indicating medical conditions experienced by individual 700, treatment information indicating treatments received by individual 700, and/or other health information. In some embodiments, external resources 500 include sources of information such as databases, websites, etc., external entities participating with system 10 (e.g., a medical records system of a health care provider that stores medical history information of patients), one or more servers outside of system 10, and/or other sources of information. In some embodiments, external resources 500 include components that facilitate communication of information such as a network (e.g., the internet), electronic storage, equipment related to Wi-Fi technology, equipment related to Bluetooth® technology, data entry devices, sensors, scanners, and/or other resources. In some embodiments, some or all of the functionality attributed herein to external resources 500 may be provided by resources included in system 10.

First client computer system 100, server computer system 200, second client computer system 300, electronic storage 400, external resources 500, and/or other components of system 10 may be configured to communicate with one another, via wired and/or wireless connections, via a network 600 (e.g., a local area network and/or the internet), via cellular technology, via Wi-Fi technology, and/or via other resources. It will be appreciated that this is not intended to be limiting, and that the scope of this disclosure includes embodiments in which these components may be operatively linked via some other communication media. In some embodiments, first client computer system 100, server computer system 200, second client computer system 300, electronic storage 400, external resources 500, and/or other components of system 10 may be configured to communicate with one another according to a client/server architecture, a peer-to-peer architecture, and/or other architectures.

First client computer system 100 may be configured to provide an interface between individual 700 and/or other users, and system 10. In some embodiments, individual first client computer system 100 is and/or is included in desktop computers, laptop computers, tablet computers, smartphones, smart wearable devices including augmented reality devices (e.g., Google Glass), wrist-worn devices (e.g., Apple Watch), and/or other computing devices associated with individual 700, and/or other users. In some embodiments, first client computer system 100 facilitates obtaining a video stream of individual 700 such that (i) physiological condition information associated with individual 700 is estimated and (ii) a 2-way video interaction between consultant 800 and individual 700 is provided. Accordingly, first client computer system 100 comprises a user interface including camera 102, microphone 104, one or more non-transitory computer-readable storage media 106 (similar to electronic storage 400 described above), processors 108, or other components. In one embodiment, the present disclosure comprises means for obtaining a live video stream of individual 700 at first client computer system 100 during a video streaming session between first client computer system 100 and second client computer system 300, with such means for obtaining taking the form of camera 102. In one embodiment, the present disclosure comprises means for storing a machine learning model on first client computer system 100, with such means for storing taking the form of non-transitory computer-readable storage media 106. Examples of other interface devices suitable for inclusion in the first client computer system 100 user interface include a touch screen, a keypad, touch sensitive or physical buttons, switches, a keyboard, knobs, levers, a display, speakers, an indicator light, an audible alarm, a printer, tactile haptic feedback device, or other interface devices. The present disclosure also contemplates that first client computer system 100 includes a removable storage interface. In this example, information may be loaded into first client computer system 100 from removable storage (e.g., a smart card, a flash drive, a removable disk, etc.) that enables caregivers or other users to customize the implementation of first client computer system 100. Other exemplary input devices and techniques adapted for use with first client computer system 100 or the user interface include an RS-232 port, RF link, an IR link, a modem (telephone, cable, etc.), or other devices or techniques.

Processor 108 is configured to provide information processing capabilities in first client computer system 100. As such, processor 108 may comprise one or more of a digital processor, an analog processor, a digital circuit designed to process information, an analog circuit designed to process information, a state machine, or other mechanisms for electronically processing information. Although processor 108 is shown in FIG. 1 as a single entity, this is for illustrative purposes only. In some embodiments, processor 108 may comprise a plurality of processing units. These processing units may be physically located within the same device (e.g., a server), or processor 108 may represent processing functionality of a plurality of devices operating in coordination (e.g., one or more servers, computing device, devices that are part of external resources 500, electronic storage 400, or other devices.)

As shown in FIG. 1, processor 108 is configured via machine-readable instructions 110 to execute one or more computer program components. The computer program components may comprise one or more of an information exchange component 112, a prediction component 114, or other components. Processor 108 may be configured to execute components 112 or 114 by software; hardware; firmware; some combination of software, hardware, or firmware; or other mechanisms for configuring processing capabilities on processor 108.

It should be appreciated that although components 112 and 114 are illustrated in FIG. 1 as being co-located within a single processing unit, in embodiments in which processor 108 comprises multiple processing units, one or more of components 112 or 114 may be located remotely from the other components. The description of the functionality provided by the different components 112 or 114 described below is for illustrative purposes, and is not intended to be limiting, as any of components 112 or 114 may provide more or less functionality than is described. For example, one or more of components 112 or 114 may be eliminated, and some or all of its functionality may be provided by other components 112 or 114. As another example, processor 108 may be configured to execute one or more additional components that may perform some or all of the functionality attributed below to one of components 112 or 114.

Information exchange component 112 is configured to store a neural network (described below) on one or more computer-readable storage media 106 of first client computer system 100. In some embodiments, information exchange component 112 is configured to obtain updated information related to an updated neural network. In some embodiments, the updated neural network is trained on other audio, image, or video data to estimate physiological conditions. In some embodiments, information exchange component 112 is configured to replace the neural network with the updated neural network such that further video data is provided to the updated neural network in lieu of the neural network to obtain further physiological condition information. In one embodiment, the present disclosure comprises means for obtaining updated information related to an updated neural network, with such means for obtaining taking the form of information exchange component 112. In one embodiment, the present disclosure comprises a means for replacing the neural network with the updated neural network, with such means for replacing taking the form of information exchange component 112.

In some embodiments, information exchange component 112 is configured to obtain a video stream (e.g., live video stream, recorded video stream, etc.) of individual 700 via camera 102 of first client computer system 100 during a time period (e.g., video streaming session between first client computer system 100 and second client computer system 300, video recording session at first client computer system 100, etc.). For example, information exchange component 112 is configured to obtain a live video stream of individual via camera 102 of first client computer 100 system during a video streaming session between first client computer system 100 and second client computer system 300. As another example, information exchange component 112 is configured to obtain a recorded video stream of individual 700 via camera 102 of first client computer system 100 during a video recording session at first client computer system 100.

In some embodiments, information exchange component 112 is configured to provide, during the time period, the physiological condition information (described below) for presentation at second client computer system 300. In some embodiments, information exchange component 112 is caused to upload the physiological condition information to server computer system 200 to provide the physiological condition information for presentation at second client computer system 300. In one embodiment, the present disclosure comprises means for providing, during a video streaming session, the physiological condition information for presentation at second client computer system 300, with such means for providing taking the form of information exchange component 112. In one embodiment, the present disclosure comprises a means for uploading the physiological condition information to server computer system 200 to provide the physiological condition information for presentation at second client computer system 300, with such means for uploading takin the form of information exchange component 112.

Prediction component 114 is configured to utilize the trained prediction model(s) (e.g., neural network(s), other machine learning model(s), etc.) and/or other information to determine physiological condition information. In some embodiments, the prediction model is trained on audio, image, or video data to estimate physiological conditions. In some embodiments, prediction component 114 is configured to utilize one or more signal processing techniques (e.g., wavelet-based detection algorithms, time delay estimation, etc.) to determine physiological condition information (e.g., heart rate, respiratory rate, SpO2, etc.). In some embodiments, video images may be processed for extraction of vital signs as described in U.S. patent application Ser. No. 14/240, 048, filed Aug. 27, 2012, entitled "CAMERA FOR GENERATING A BIOMETRICAL SIGNAL OF A LIVING BEING", the content of which is incorporated herein in its entirety by reference.

In some embodiments, prediction component 114 is configured to provide, during a time period (e.g., video streaming session, video recording session, etc.), video data of the video stream (e.g., live video stream, recorded video stream, etc.) as input to the prediction model to obtain physiological condition information from the prediction model. In some embodiments, the physiological condition information indicates one or more physiological conditions of individual 700. In some embodiments, prediction component 114 is configured to cause the trained prediction model to output, during the time period (e.g., during the video streaming session, during the video recording session, etc.) prediction model responses to at least some of video data of the video stream (e.g., live video stream, recorded video stream, etc.) by providing the at least some of video data of the video stream obtained during the time period as input to the trained prediction model. In some embodiments, the prediction model responses are based on analysis of one or more colored signals of the video data. In some embodiments, the prediction model responses one or more biometrical signals (e.g., vital signs). In one embodiment, the present disclosure comprises means for providing, during a video streaming session, video data of a live video stream as input to the machine learning model to obtain physiological condition information from the machine learning model, with such means for providing taking the form of the prediction component 114.

For example, prediction component 114 may provide, during a video streaming session, video data of a live video stream as input to the prediction model to obtain physiological condition information from the prediction model. As another example, prediction component 114 may provide, during a video recording session, video data of a recorded video stream as input to the prediction model to obtain physiological condition information from the prediction model. In some embodiments, physiological information may be extracted from detected electromagnetic radiation emitted or reflected by a subject as described in U.S. patent application Ser. No. 14/079,668, filed on Nov. 14, 2013, entitled "DEVICE AND METHOD FOR EXTRACTING PHYSIOLOGICAL INFORMATION" (issued as U.S. Pat. No. 9,770,197 on Sep. 26, 2017), the content of which is incorporated herein in its entirety by reference.

In some embodiments, prediction component 114 is configured such that the prediction model estimates one or more of the individual's emotion, changes in the individual's voice patterns, or other information based on the prediction model's audio data training. In some embodiments, prediction component 114 is configured such that the prediction model estimates one or more of the individual's pulse, the individual's respiration rate, the individual's SpO2, the individual's difficulty breathing, the individual's shaking and/or shivering, changes in the individual's skin color, changes in the individual's pupil size, the individual's facial asymmetry, or other information based on the prediction model's video data training. In some embodiments, prediction component 114 is configured to determine individual 700's vital signs (e.g., hear rate, respiratory rate, SpO2, etc.) by determining (i) one or more changes in the color of the face of individual 700 during one or more cardiac cycles and (ii) chest wall movements. In some embodiments, vital sign information of a subject may be determined while the subject is illuminated with radiation as described in U.S. patent application Ser. No. 14/192,905, filed Feb. 28, 2014, entitled "SYSTEM AND METHOD FOR DETERMINING VITAL SIGN INFORMATION", the content of which is incorporated herein in its entirety by reference.

In some embodiments, prediction component 114 is configured to detect one or more of emotional stress, pain, or other information during the time period. For example, prediction component 114 may monitor individuals who are recovering post-operatively or suffer from conditions leading to chronic pain for stress levels and present the results to consultant 800 during the video streaming session. In some embodiments, prediction component 114 is configured to, based on the trained prediction model outputs, detect one or more of changes in pupil diameter as individual 700 speaks, facial expressions revealing pain and stress, changes in vitals reflecting pain (e.g., a variability in heart rate and breathing), changes in voice and tone due to stress and pain, flushing in a part of the face of individual 700, or other symptoms.

In some embodiments, prediction component 114 is configured to, based on the trained prediction model outputs, detect physiological changes experienced by individual 700. In some embodiments, prediction component 114 is configured to changes in facial symmetry (e.g., as individual 700 speaks). In some embodiments, a shift of the mouth may indicate facial paralysis, one of the symptoms of a stroke. In case of a stroke, paralysis tends to preserve the upper half of the face, and individual 700 may be able to frown and raise eyebrows. Accordingly, prediction component 114 may detect mouth diversions in response to a request (e.g., by consultant 800) for a smile, a whistle, etc. In some embodiments, prediction component 114 is configured to obtain physiological condition information of individual 700 by automatically detecting shaking and shivering during the time period. In some embodiments, prediction component 114 is configured to, based on previously obtained/recorded video streams, determine whether individual 700 shows any irregular shaking or shivering.

In some embodiments, prediction component 114 is configured to determine, based on the estimated vital signs, individual 700's cardiac rhythm and identify "regularly irregular" and "irregularly irregular" heart rhythms. Such a determination may facilitate screening for intermittent atrial fibrillation (a-fib) which may be a risk factor for stroke. In some embodiments, prediction component 114 is configured to determine, during the time period (e.g., video streaming session between first client computer system 100 and second client computer system 300) irregular heart rhythms by utilizing a continuous plethysmography obtained by, for example, continuously monitoring blood oxygen levels. In some embodiments, blood oxygen saturation of a subject may be determined as described in U.S. patent application Ser. No. 14/135,644, filed Dec. 20, 2013, entitled "DEVICE AND METHOD FOR DETERMINING THE BLOOD OXYGEN SATURATION OF A SUBJECT" (issued as U.S. Pat. No. 9,125,606 on Sep. 8, 2015), the content of which is incorporated herein in its entirety by reference.

In some embodiments, prediction component 114 is configured to determine, via the trained prediction model, one or more changes in vital signs in response to consultant 800 instructions for individual 700 to perform an activity. For example, individual 700 may be asked to move an arm or a limb that is causing pain in order for prediction component 114 to objectively measure the effect of this action on individual 700's vitals and pain response. As another example, individual 700 may be asked to perform task requiring physical effort in order for prediction component 114 to determine its effect on breathing and pulse.

With the variation of lighting conditions in individual 700's home, it may be difficult to perform an objective and automated assessment of skin color. In addition, video streams may be at different times of the day. In some embodiments, prediction component 114 is configured to automatically calibrate the video stream's color data based on a fixed color in the video stream. For example, prediction component 114 may calibrate the video stream's color data based on a pendant or a badge worn by individual 700. In some embodiments, prediction component 114 is configured to determine an identity of individual 700 via (i) facial recognition, (ii) iris and/or retina recognition, (iii) cardiac rhythms, (iv) palm vein patterns, or other biometric signatures.

Server computer system 200 is configured to provide computational capabilities to system 10. In some embodiments, server computer system is configured to receive physiological condition information (e.g., from information exchange component 112) and provide the physiological condition information for presentation at second client computer system 300. In some embodiments, server computer system is configured to train the prediction model on a periodic basis, in accordance with a schedule, or based on other automated triggers. In some embodiments, server computer system facilitates monitoring of vital signs and initiates a live video stream in response to one or more vital signs exceeding a predetermined threshold. Accordingly, server computer system comprises processors 208 or other components.

Processor 208 is configured to provide information processing capabilities in server computer system 200. As such, processor 208 may comprise one or more of a digital processor, an analog processor, a digital circuit designed to process information, an analog circuit designed to process information, a state machine, or other mechanisms for electronically processing information. Although processor 208 is shown in FIG. 1 as a single entity, this is for illustrative purposes only. In some embodiments, processor 208 may comprise a plurality of processing units. These processing units may be physically located within the same device (e.g., a server), or processor 208 may represent processing functionality of a plurality of devices operating in coordination (e.g., one or more servers, other client computer systems, devices that are part of external resources 500, electronic storage 400, or other devices.)

As shown in FIG. 1, processor 208 is configured via machine-readable instructions 210 to execute one or more computer program components. The computer program components may comprise one or more of a communications component 212, a vital sign analysis component 214, a prediction model update component 216, or other components. Processor 208 may be configured to execute components 212, 214, or 216 by software; hardware; firmware; some combination of software, hardware, or firmware; or other mechanisms for configuring processing capabilities on processor 208.

It should be appreciated that although components 212, 214, and 216 are illustrated in FIG. 1 as being co-located within a single processing unit, in embodiments in which processor 208 comprises multiple processing units, one or more of components 212, 214, or 216 may be located remotely from the other components. The description of the functionality provided by the different components 212, 214, or 216 described below is for illustrative purposes, and is not intended to be limiting, as any of components 212, 214, or 216 may provide more or less functionality than is described. For example, one or more of components 212, 214, or 216 may be eliminated, and some or all of its functionality may be provided by other components 212, 214, or 216. As another example, processor 208 may be configured to execute one or more additional components that may perform some or all of the functionality attributed below to one of components 212, 214, or 216.

Communications component 212 is configured to receive, from information exchange component 112, the physiological condition information for presentation at second client computer system 300. In some embodiments, communications component 212 is configured to receive, during the video recording session, the recorded video stream and the physiological condition information (e.g., as determined by prediction component 114). In some embodiments, communications component 212 is configured to responsive to the physiological condition information exceeding a predetermined threshold, initiate a live video streaming session between the first client computer system and the second client computer system. For example, individual 700 may record their video as a message that consultant 800 may view at a later time. The video may be analyzed by prediction component 114 in order to automatically determine vitals as well as physiological irregularities. In some embodiments, responsive to (i) consultant 800 being unavailable during the time period in which individual 700 recorded their video and (ii) one or more of the physiological condition information exceeding a predetermined threshold (e.g., as determined by vital sign analysis component 214), communications component 212 may initiate a live video streaming session between individual 700 (via first client computer system 100) and consultant 800 (via second client computer system 300). In one embodiment, the present disclosure comprises a means for receiving, during a video recording session, the recorded video stream and the physiological condition information, with such means for receiving taking the form of communications component 212. In one embodiment, the present disclosure comprises a means for initiating a live video streaming session between first client computer system 100 and second client computer system 300, with such means for initiating taking the form of communications component 212.

Vital sign analysis component 214 is configured to determine, during the video recording session, whether the physiological condition information exceeds a predetermined threshold. For example, vital sign analysis component 214 may, based on previously obtained/recorded videos, determine whether individual 700 is experiencing any irregular shaking or shivering. In one embodiment, the present disclosure comprises a means for determining, during a video recording session, whether the physiological condition information exceeds a predetermined threshold, with such means for determining taking the form of vital sign analysis component 214.

In some embodiments, vital sign analysis component 214 is configured to plot different physiological information features over time to detect deterioration or improvement. For example, vital sign analysis component 214 may plot vital signs versus weeks after surgery. In some embodiments, vital sign analysis component 214 causes the plots to be displayed on second client computer system 300 with one or more relevant contextual features. The one or more relevant contextual information may include one or more of existing chronic conditions (atrial fibrillation, diabetes, etc.), current medications, or other information.

Prediction model update component 216 is configured to cause the prediction model to be trained on audio, image, or video data to estimate physiological conditions. In some embodiments, prediction model update component is configured to retrain the prediction model at any time (e.g., continuously, prior to commencement of video stream session, subsequent to the video stream session, every day, responsive to a change in the physiological condition information, and/or any other period). In some embodiments, prediction model update component 216 is configured to train the prediction model based on historical information related to the one or more physiological conditions of individual by providing the historical information related to the one or more physiological conditions of the patient as input to the prediction model. In some embodiments, prediction model update component 216 is configured to train the prediction model based on one or more of other individuals' (e.g., other patients) physiological condition information, other individuals' audio, image, or video data, or other information.

Second client computer system 300 is configured to provide an interface between consultant 800 and/or other users, and system 10. In some embodiments, second client computer system 300 is and/or is included in desktop computers, laptop computers, tablet computers, smartphones, smart wearable devices including augmented reality devices (e.g., Google Glass) and wrist-worn devices (e.g., Apple Watch), and/or other computing devices associated with consultant 800, and/or other users. In some embodiments, second client computer system 300 is, and/or is included in equipment used in hospitals, doctor's offices, and/or other facilities. Second client computer system 300 is configured to provide information to and/or receive information from individual 700, consultant 800, and/or other users. For example, second client computer system 300 is configured to present a graphical user interface 302 to consultant 800 and/or other users to facilitate presentation of the video stream of individual 700 and their physiological condition information. In some embodiments, graphical user interface 302 includes a plurality of separate interfaces associated with second client computer system 300 and/or other components of system 10; multiple views and/or fields configured to convey information to and/or receive information from individual 700, consultant 800, and/or other users; and/or other interfaces. Accordingly, second client computer system 300 comprises user interface 302, processors 308, and/or other components.

Examples of interface devices suitable for inclusion in user interface 302 include a camera, a touch screen, a keypad, touch sensitive or physical buttons, switches, a keyboard, knobs, levers, a display, speakers, a microphone, an indicator light, an audible alarm, a printer, tactile haptic feedback device, or other interface devices. The present disclosure also contemplates that second client computer system 300 includes a removable storage interface. In this example, information may be loaded into second client computer system 300 from removable storage (e.g., a smart card, a flash drive, a removable disk, etc.) that enables consultant 800 or other users to customize the implementation of second client computer system 300. Other exemplary input devices and techniques adapted for use with second client computer system 300 or the user interface include an RS-232 port, RF link, an IR link, a modem (telephone, cable, etc.), or other devices or techniques.

Processor 308 is configured to provide information processing capabilities in second client computer system 300. As such, processor 308 may comprise one or more of a digital processor, an analog processor, a digital circuit designed to process information, an analog circuit designed to process information, a state machine, or other mechanisms for electronically processing information. Although processor 308 is shown in FIG. 1 as a single entity, this is for illustrative purposes only. In some embodiments, processor 308 may comprise a plurality of processing units. These processing units may be physically located within the same device (e.g., a server), or processor 308 may represent processing functionality of a plurality of devices operating in coordination (e.g., one or more servers, other client computer systems, devices that are part of external resources 500, electronic storage 400, or other devices.)

As shown in FIG. 1, processor 308 is configured via machine-readable instructions 310 to execute one or more computer program components. The computer program components may comprise one or more of a data reception component 312, a presentation component 314, or other components. Processor 308 may be configured to execute components 312 or 314 by software; hardware; firmware; some combination of software, hardware, or firmware; or other mechanisms for configuring processing capabilities on processor 308.

It should be appreciated that although components 312 and 314 are illustrated in FIG. 1 as being co-located within a single processing unit, in embodiments in which processor 308 comprises multiple processing units, one or more of components 312 or 314 may be located remotely from the other components. The description of the functionality provided by the different components 312 or 314 described below is for illustrative purposes, and is not intended to be limiting, as any of components 312 or 314 may provide more or less functionality than is described. For example, one or more of components 312 or 314 may be eliminated, and some or all of its functionality may be provided by other components 312 or 314. As another example, processor 308 may be configured to execute one or more additional components that may perform some or all of the functionality attributed below to one of components 312 or 314.

Data reception component 312 is configured to receive, during the time period, a live view of a real-world environment. In some embodiments, the live view of the real-world environment includes the video stream of individual 700. For example, data reception component 700 receives, during the video streaming session, a live view of a real-world environment (e.g., the live video stream of the individual). In one embodiment, the present disclosure comprises means for receiving, during the video streaming session, a live view of a real-world environment, with such means for receiving taking the form of data reception component 312.

In some embodiments, data reception component 312 is configured to receive, during the time period, the physiological condition information (e.g., from communications component). For example, data reception component is configured to receive, during the video streaming session, the physiological condition information. In one embodiment, the present disclosure comprises a means for receiving, during the video streaming session, the physiological condition information, with such means for receiving taking the form of data reception component 312.

Presentation component 314 is configured to provide, via user interface 302, the physiological condition information for presentation at second client computer system 300. In some embodiments, the physiological condition information is obtained based on the prediction model responses to at least some of the video data of the live video stream (e.g., during a video streaming session). In some embodiments, the physiological condition information is obtained based on the prediction model responses to at least some of the video data of the recorded video stream (e.g., during a video recording session). In some embodiments, the physiological condition information presented includes one or more vital signs.

Figure 3:
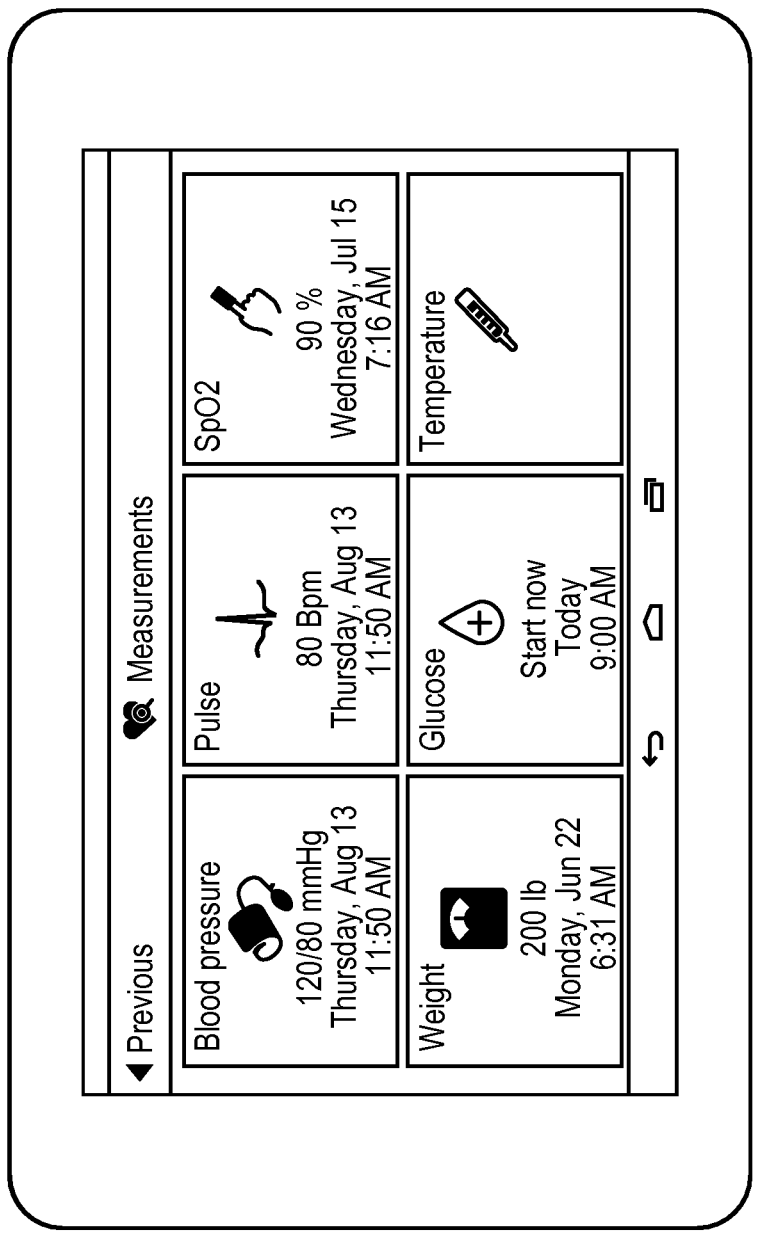
FIG. 3 illustrates a traditional user interface for viewing patient vital signs, in accordance with one or more embodiments.

Traditionally, vital sign measurement data observation may require that consultant 800 turn their attention from individual 700 to the data, which may result in several visual signs and/or features of individual 700 being missed during the data review period. Additionally, untrained professionals could miss subtle changes in skin color, voice and behavior patterns if they see individual 700 for the first time via video. By way of a non-limiting example, FIG. 3 illustrates a traditional user interface for viewing patient vital signs, in accordance with one or more embodiments. As shown in FIG. 3, one or more vital signs (e.g., live measurement data, previously measured vital signs) may be presented on a user interface. In this example, a clinician may not be provided with a visual representation of individual 700 at the review period, during which facial expressions or other visual symptoms could be missed.

Returning to FIG. 1, presentation component 314 is configured to generate augmented reality content based on the received physiological condition information and overlay the augmented reality content on the live view of the real-world environment for presentation at second client computer system 300. The augmented reality presentation may, for example, comprise a live view of the real-world environment and one or more augmentations to the live view. The live view may comprise the live video stream of the individual. The augmentations may comprise content provided by prediction component 114 (e.g., one or more physiological conditions of the individual), other content related to one or more aspects in the live view, or other augmentations.

As an example, the augmented reality content may comprise visual or audio content (e.g., text, images, audio, video, etc.) generated at second client computer system 300 or a remote computer system based on the one or more physiological conditions of the individual (e.g., as determined by prediction component 114), and presentation component 314 may obtain the augmented reality content from second client computer system 300 or the remote computer system. In some embodiments, presentation component 314 may overlay, in the augmented reality presentation, the augmented reality content on a live view of the real-world environment. In an embodiment, the presentation of the augmented reality content (or portions thereof) may occur automatically, but may also be "turned off" by a user (e.g., by manually hiding the augmented reality content or portions thereof after it is presented, by setting preferences to prevent the augmented reality content or portions thereof from being automatically presented, etc.). As an example, consultant 800 may choose to reduce the amount of automatically-displayed content via user preferences (e.g., by selecting the type of information consultant 800 desires to be automatically presented, by selecting the threshold amount of information that is to be presented at a given time, etc.). In one embodiment, the present disclosure comprises a means for generating, during the video streaming session, augmented reality content based on the received physiological condition information, with such means for generating taking the form of presentation component 314. In one embodiment, the present disclosure comprises a means for overlaying the augmented reality content on the live view of the real-world environment for presentation at second client computer system 300 during a video streaming session, with such means for overlaying taking the form of presentation component 314.

Figure 4:
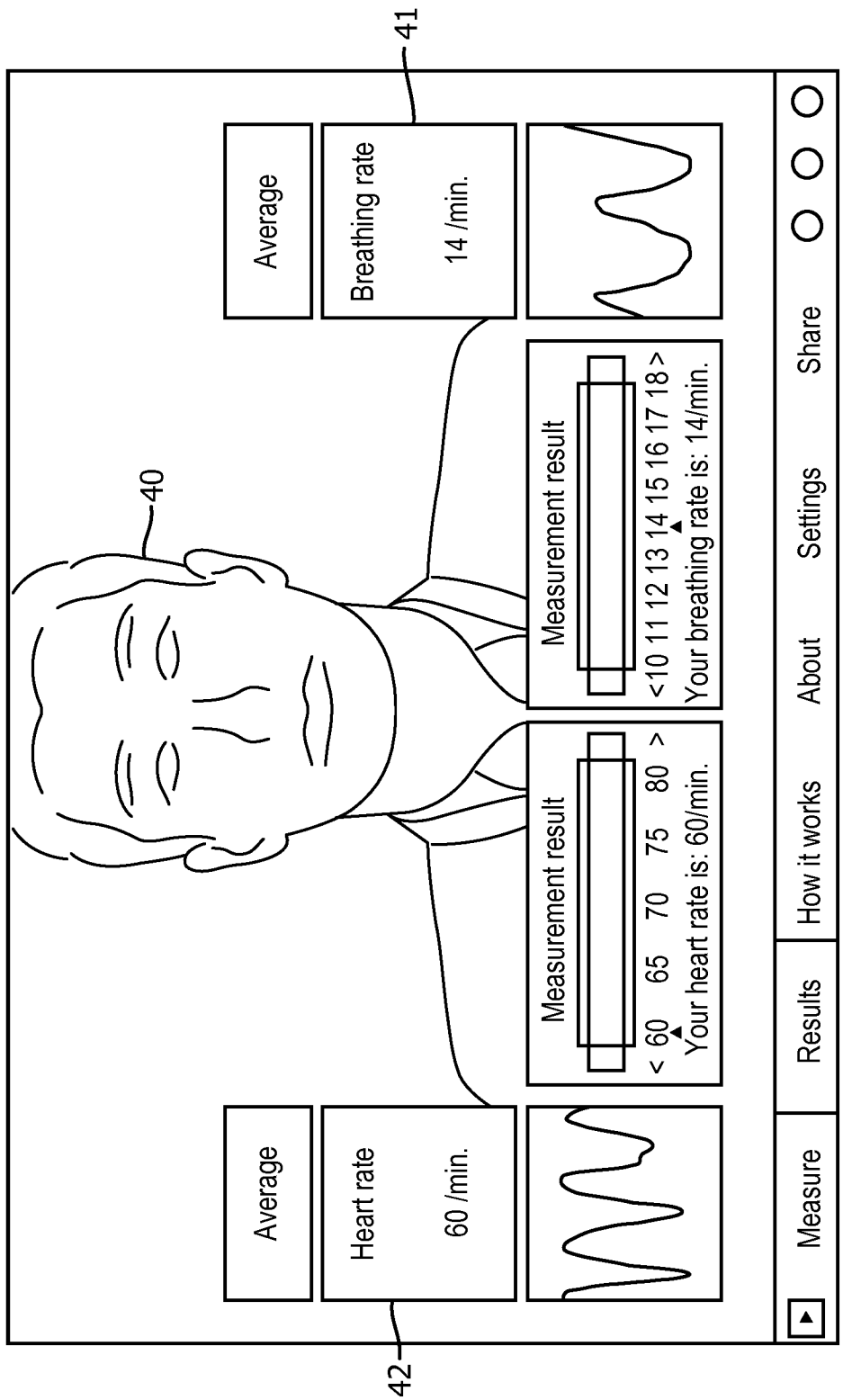
FIG. 4 illustrates overlay of vital signs onto a live video stream, in accordance with one or more embodiments

In some embodiments, presentation component 34 is configured to output the augmented-reality-enhanced view on user interface 302 (e.g., a display screen) or on any other user interface device. By way of a non-limiting example, FIG. 4 illustrates overlay of vital signs onto a live video stream 40, in accordance with one or more embodiments. As shown in FIG. 4, one or more vital signs (e.g., respiratory rate 41, pulse 42, pulse oximetry) are displayed in real time as an individual is speaking to a consultant. In this example, the consultant may measure one or more vital signs, observe changes in the one or more vital signs, observe changes in the appearance of the individual, or take other actions while speaking to the individual or asking questions from the individual.

Figure 5:
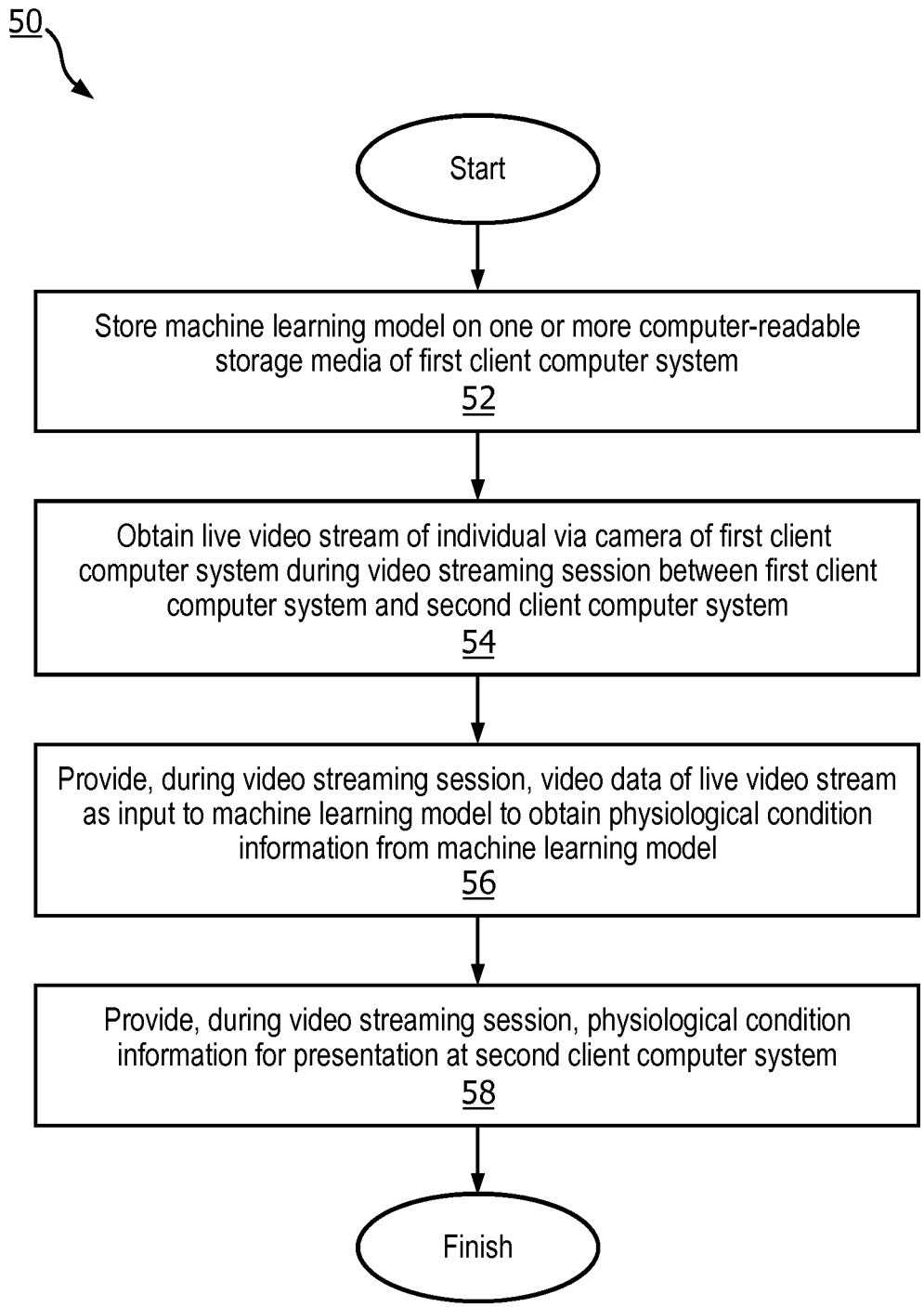
FIG. 5 illustrates a method of providing client-side physiological condition estimations during a live video session, in accordance with one or more embodiments.

FIG. 5 illustrates a method of providing client-side physiological condition estimations during a live video session, in accordance with one or more embodiments. Method 50 may be performed with a system. The system comprises a first client computer system, a server computer system, a second client computer system, or other components. The first client computer system includes one or more processors. The processors are configured by machine readable instructions to execute computer program components. The computer program components include an information exchange component, a prediction component, or other components. The operations of method 50 presented below are intended to be illustrative. In some embodiments, method 50 may be accomplished with one or more additional operations not described, or without one or more of the operations discussed. Additionally, the order in which the operations of method 50 are illustrated in FIG. 5 and described below is not intended to be limiting.

In some embodiments, method 50 may be implemented in one or more processing devices (e.g., a digital processor, an analog processor, a digital circuit designed to process information, an analog circuit designed to process information, a state machine, or other mechanisms for electronically processing information). The devices may include one or more devices executing some or all of the operations of method 50 in response to instructions stored electronically on an electronic storage medium. The processing devices may include one or more devices configured through hardware, firmware, or software to be specifically designed for execution of one or more of the operations of method 50.

At an operation 52, a machine learning model is stored on one or more computer-readable storage media of a first client computer system. In some embodiments, the machine learning model is trained on audio, image, or video data to estimate physiological conditions. In some embodiments, operation 52 is performed by a processor component the same as or similar to information exchange component 112 (shown in FIG. 1 and described herein).

At an operation 54, a live video stream of an individual is obtained via a camera of the first client computer system during a video streaming session between the first client computer system and a second client computer system. In some embodiments, operation 54 is performed by a processor component the same as or similar to information exchange component 112 (shown in FIG. 1 and described herein).

At an operation 56, video data of the live video stream is provided, during the video streaming session, as input to the machine learning model to obtain physiological condition information from the machine learning model. In some embodiments, the physiological condition information indicate one or more physiological conditions of the individual. In some embodiments, operation 56 is performed by a processor component the same as or similar to prediction component 114 (shown in FIG. 1 and described herein).

At an operation 58, the physiological condition information is provided, during the video streaming session, for presentation at the second client computer system. In some embodiments, operation 58 is performed by a processor component the same as or similar to information exchange component 112 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to provide client-side physiological condition estimations during a live video session, the system comprising:
a first client computer system comprising a camera, one or more computer-readable storage media, and one or more first processors configured by machine readable instructions that cause the first client computer system to:

store a neural network on the one or more computer-readable storage media of the first client computer system, the neural network being trained on audio, image, or video data to estimate physiological conditions;

obtain a live video stream of an individual via the camera during a video streaming session between the first client computer system and a second client computer system;

provide, during the video streaming session, video data of the live video stream as input to the neural network to obtain physiological condition information from the neural network, the physiological condition information indicating one or more physiological conditions of the individual, wherein the neural network is configured to automatically generate program instructions to calibrate the video data based on a fixed color in the live video stream; and provide, during the video streaming session, the physiological condition information for presentation at the second client computer system.

2. The system of claim 1, wherein the first client computer system is caused to:

obtain updated information related to an updated neural network, the updated neural network being trained on other audio, image, or video data to estimate physiological conditions; and replace the neural network with the updated neural network such that further video data is provided to the updated neural network in lieu of the neural network to obtain further physiological condition information.

3. The system of claim 1, wherein the first client computer system is caused to upload the physiological condition information to a server computer system to provide the physiological condition information for presentation at the second client computer system.

4. The system of claim 3, wherein the second client computer system comprises one or more second processors configured by machine readable instructions that cause the second client computer system to:

receive, during the video streaming session, a live view of a real-world environment, the live view of the real-world environment comprising the live video stream of the individual;

receive, during the video streaming session, the physiological condition information;

generate, during the video streaming session, augmented reality content based on the received physiological condition information; and overlay the augmented reality content on the live view of the real-world environment for presentation during the video streaming session.

5. The system of claim 3, wherein the first client computer system is caused to:

obtain a recorded video stream of the individual via the camera of the first client computer system during a video recording session at the first client computer system; and provide, during the video recording session, video data of the recorded video stream as input to the neural network to obtain physiological condition information from the neural network; and wherein server computer system comprises one or more server processors configured by machine readable instructions that cause the server computer system to:

receive, during the video recording session, the recorded video stream and the physiological condition information; and determine, during the video recording session, whether the physiological condition information exceeds a predetermined threshold; and responsive to the physiological condition information exceeding a predetermined threshold, initiate a live video streaming session between the first client computer system and the second client computer system.

6. The system of claim 1, wherein the neural network estimates one or both of the individual's emotion or changes in the individual's voice patterns based on the neural network's audio data training, and wherein the neural network estimates one or more of the individual's pulse, the individual's respiration rate, the individual's SpO2, the individual's difficulty breathing, the individual's shaking and/or shivering, changes in the individual's skin color, changes in the individual's pupil size, or the individual's facial asymmetry based on the neural network's video data training.

7. A method of providing client-side physiological condition estimations during a live video session, the method comprising:

storing a machine learning model on one or more computer-readable storage media of a first client computer system, the machine learning model being trained on audio, image, or video data to estimate physiological conditions;

obtaining a live video stream of an individual via a camera of the first client computer system during a video streaming session between the first client computer system and a second client computer system;

providing, during the video streaming session, video data of the live video stream as input to the machine learning model to obtain physiological condition information from the machine learning model, the physiological condition information indicating one or more physiological conditions of the individual, wherein the neural network is configured to automatically generate program instructions to calibrate the video data based on a fixed color in the live video stream; and providing, during the video streaming session, the physiological condition information for presentation at the second client computer system.

8. The method of claim 7, further comprising:

obtaining, with the first client computer system, updated information related to an updated neural network, the updated neural network being trained on other audio, image, or video data to estimate physiological conditions; and replacing, with the first client computer system, the neural network with the updated neural network such that further video data is provided to the updated neural network in lieu of the neural network to obtain further physiological condition information.

9. The method of claim 7, further comprising:

uploading, with the first client computer system, the physiological condition information to a server computer system to provide the physiological condition information for presentation at the second client computer system.

10. The method of claim 9, further comprising:

receiving, with the second client computer system and during the video streaming session, a live view of a real-world environment, the live view of the real-world environment comprising the live video stream of the individual;

receiving, with the second client computer system and during the video streaming session, the physiological condition information;

generating, with the second client computer system and during the video streaming session, augmented reality content based on the received physiological condition information; and overlaying, with the second client computer system, the augmented reality content on the live view of the real-world environment for presentation at the second client computer system during the video streaming session.

11. The method of claim 9, further comprising:

obtaining a recorded video stream of the individual via the camera of the first client computer system during a video recording session at the first client computer system;

providing, with the first client computer system and during the video recording session, video data of the recorded video stream as input to the machine learning model to obtain physiological condition information from the machine learning model;

receiving, with the server computer system and during the video recording session, the recorded video stream and the physiological condition information;

determining, with the server computer system and during the video recording session, whether the physiological condition information exceeds a predetermined threshold; and responsive to the physiological condition information exceeding a predetermined threshold, initiating, with the server computer system, a live video streaming session between the first client computer system and the second client computer system.

12. The method of claim 7, wherein the machine learning model estimates one or both of the individual's emotion or changes in the individual's voice patterns based on the machine learning model's audio data training, and wherein the machine learning model estimates one or more of the individual's pulse, the individual's respiration rate, the individual's SpO2, the individual's difficulty breathing, the individual's shaking and/or shivering, changes in the individual's skin color, changes in the individual's pupil size, or the individual's facial asymmetry based on the machine learning model's video data training.

13. A system for providing client-side physiological condition estimations during a live video session, the system comprising:

one or more computer processors;
one or more computer readable storage devices;
program instructions stored on the one or more computer readable storage devices for execution by at least one of the one or more computer processors, the stored program instructions comprising:
program instructions to store a machine learning model on a first client computer system, the machine learning model being trained on audio, image, or video data to estimate physiological conditions;
program instructions to obtain a live video stream of an individual at the first client computer system during a video streaming session between the first client computer system and a second client computer system;
program instructions to provide, during the video streaming session, video data of the live video stream as input to the machine learning model to obtain physiological condition information from the machine learning model, the physiological condition information indicating one or more physiological conditions of the individual, wherein the neural network is configured to automatically generate program instructions to calibrate the video data based on a fixed color in the live video stream; and program instructions to provide, during the video streaming session, the physiological condition information for presentation at the second client computer system.

14. The system of claim 13, further comprising:

program instructions to obtain updated information related to an updated neural network, the updated neural network being trained on other audio, image, or video data to estimate physiological conditions; and program instructions to replace the neural network with the updated neural network such that further video data is provided to the updated neural network in lieu of the neural network to obtain further physiological condition information.

15. The system of claim 13, further comprising:

program instructions to upload the physiological condition information to a server computer system to provide the physiological condition information for presentation at the second client computer system.

16. The system of claim 15, further comprising:

program instructions to receive, during the video streaming session, a live view of a real-world environment, the live view of the real-world environment comprising the live video stream of the individual;

program instructions to receive, during the video streaming session, the physiological condition information;

program instructions to generate, during the video streaming session, augmented reality content based on the received physiological condition information; and program instructions to overlay the augmented reality content on the live view of the real-world environment for presentation at the second client computer system during the video streaming session.

17. The system of claim 15, further comprising:

program instructions to obtain a recorded video stream of the individual during a video recording session at the first client computer system;

program instructions to provide, during the video recording session, video data of the recorded video stream as input to the machine learning model to obtain physiological condition information from the machine learning model;

program instructions to receive, during the video recording session, the recorded video stream and the physiological condition information;

program instructions to determine, during the video recording session, whether the physiological condition information exceeds a predetermined threshold; and responsive to the physiological condition information exceeding a predetermined threshold, program instructions to initiate a live video streaming session between the first client computer system and the second client computer system.

18. The system of claim 13, wherein the machine learning model estimates one or both of the individual's emotion or changes in the individual's voice patterns based on the machine learning model's audio data training, and wherein the machine learning model estimates one or more of the individual's pulse, the individual's respiration rate, the individual's SpO2, the individual's difficulty breathing, the individual's shaking and/or shivering, changes in the individual's skin color, changes in the individual's pupil size, or the individual's facial asymmetry based on the machine learning model's video data training.

* * * * *